(12) United States Patent

Yamauchi et al.

(10) Patent No.: US 10,646,596 B2
(45) Date of Patent: May 12, 2020

(54) NEAR-INFRARED DYE-BOUND TRANSFERRIN, AND CONTRAST AGENT FOR PHOTOACOUSTIC IMAGING, INCLUDING THE NEAR-INFRARED DYE-BOUND TRANSFERRIN

(71) Applicant: CANON KABUSHIKI KAISHA, Tokyo (JP)

(72) Inventors: Fumio Yamauchi, Kyoto (JP); Kengo Kanazaki, Kyoto (JP); Satoshi Ogawa, Kyoto (JP)

(73) Assignee: CANON KABUSHIKI KAISHA, Tokyo (JP)

(*) Notice: Subject to any disclaimer, the term of this patent is extended or adjusted under 35 U.S.C. 154(b) by 741 days.

(21) Appl. No.: 15/070,405

(22) Filed: Mar. 15, 2016

(65) Prior Publication Data

US 2016/0279271 A1  Sep. 29, 2016

(30) Foreign Application Priority Data

Mar. 23, 2015  (JP) ................. 2015-059617

(51) Int. Cl.
A61K 49/00 (2006.01)
A61K 49/22 (2006.01)

(52) U.S. Cl.
CPC ........ *A61K 49/221* (2013.01); *A61K 49/0034* (2013.01); *A61K 49/0056* (2013.01); *A61K 49/005* (2013.01); *A61K 49/0043* (2013.01)

(58) Field of Classification Search
None
See application file for complete search history.

(56) References Cited

U.S. PATENT DOCUMENTS

| | | | | |
|---|---|---|---|---|
| 6,974,873 B2* | 12/2005 | Leung | ............... | A61K 41/0057 548/455 |
| 7,468,177 B2* | 12/2008 | Achilefu | ............. | A61K 31/403 424/1.11 |
| 7,865,230 B1* | 1/2011 | Sevick-Muraca | .... | A61B 5/0091 600/473 |
| 9,138,492 B2 | 9/2015 | Fukui et al. | | |
| 2002/0037254 A1 | 3/2002 | Sinn et al. | | |
| 2003/0143159 A1 | 7/2003 | Achilefu et al. | | |
| 2005/0019263 A1 | 1/2005 | Sinn et al. | | |
| 2008/0317676 A1 | 12/2008 | Rajopadhye et al. | | |
| 2010/0022449 A1* | 1/2010 | Achilefu | ............ | A61K 49/0021 514/1.1 |
| 2011/0027191 A1 | 2/2011 | Dow et al. | | |
| 2013/0209367 A1 | 8/2013 | Ito et al. | | |
| 2013/0323178 A1 | 12/2013 | Yamauchi et al. | | |
| 2015/0071861 A1 | 3/2015 | Kondo et al. | | |
| 2015/0157741 A1 | 6/2015 | Yamauchi et al. | | |
| 2015/0165071 A1 | 6/2015 | Takahashi et al. | | |
| 2015/0290345 A1 | 10/2015 | Takahashi et al. | | |

FOREIGN PATENT DOCUMENTS

WO   2014/013729 A1   1/2014

OTHER PUBLICATIONS

Pham et al. (Bioconj. Chem. 2003, 14, 1048-1051).*
Licha et al. (Proc. SPIE 3600, Biomedical Imaging: Reporters, Dyes, and Instrumentation, (Jul. 2, 1999).*
Muguruma, Naoki & Takayama, Tetsuji (2011) Endoscopic Molecular Imaging in Gastrointestinal Oncology.*
Andreas Becker et al., "Macromolecular Contrast Agents for Optical Imaging of Tumors: Comparison of Indotricarbocyanine-labeled Human Serum Albumin and Transferrin," 72(2) Photochem. Photobiol. 234-241 (Aug. 2000).
Liang Shan et al., "Dual Probe with Fluorescent and Magnetic Properties for Imaging Solid Tumor Xenografts," 6(2) Mol. Imaging 85-95 (Mar. 2007).
Jun Yue et al., "Transferrin-Conjugated Micelles: Enhanced Accumulation and Antitumor Effect for Transferrin-Receptor-Overexpressing Cancer Models," 9(7) Mol. Pharmaceutics 1919-1931 (May 2012) (XP55293341).
Extended European Search Report in European Application No. 16161397.1 (dated Aug. 12, 2016).
Notification of Reasons for Refusal in priority Japanese Application No. 2015-059617 (dated Feb. 21, 2019).
Xiu-feng Zhang et al., "Spectroscopic and Molecular Modeling Study of Cyanine Dye Interacting with Human Serum Transferrin," 469 Colloids and Surfaces A: Physicochem. Eng. Aspects 187-193 (Jan. 2015).
Elizabeth M. McCorquodale et al., "Indocyanine Green as a Noncovalent, Pseudofluorogenic Label for Protein Determination by Capillary Electrophoresis," 22(12) Electrophoresis 2403-2408 (Aug. 2001).
First Office Action in Chinese Application No. 201610167994.5 (dated Jan. 28, 2019).

* cited by examiner

Primary Examiner — Michael G. Hartley
Assistant Examiner — Melissa J Perreira
(74) Attorney, Agent, or Firm — Venable LLP

(57) ABSTRACT

A novel near-infrared dye-bound transferrin exhibiting a high absorption coefficient in the near-infrared wavelength region, a high tumor accumulation property, a high tumor/blood ratio and a high imaging contrast, and a contrast agent for photoacoustic imaging, including the same are provided. A compound is provided in which transferrin and an organic dye having a specified structure that absorbs light in the near-infrared wavelength region are covalently bound.

6 Claims, 1 Drawing Sheet

Specification includes a Sequence Listing.

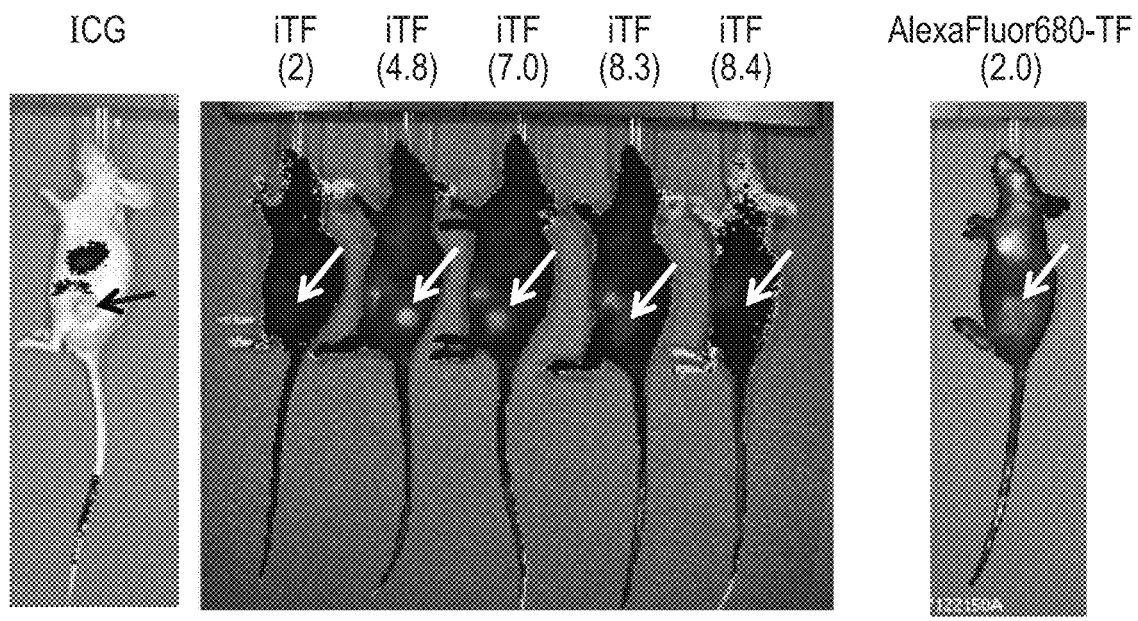

SEQUENCE LISTING

<160> NUMBER OF SEQ ID NOS: 1

<210> SEQ ID NO 1
<211> LENGTH: 698
<212> TYPE: PRT
<213> ORGANISM: Homo sapiens

<400> SEQUENCE: 1

```
Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Ile Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
        355                 360                 365
```

```
His Glu Arg Leu Lys Cys Asp Glu Trp Ser Val Asn Ser Val Gly Lys
        370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Gly Ala Gly Tyr Phe Ala Val
        435                 440                 445

Ala Val Val Lys Lys Ser Ala Ser Asp Leu Thr Trp Asp Asn Leu Lys
    450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
                500                 505                 510

Leu Cys Lys Leu Cys Met Gly Ser Gly Leu Asn Leu Cys Glu Pro Asn
        515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
                580                 585                 590

Tyr Ala Asn Cys His Leu Ala Arg Ala Pro Asn His Ala Val Val Thr
            595                 600                 605

Arg Lys Asp Lys Glu Ala Cys Val His Lys Ile Leu Arg Gln Gln Gln
        610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
        675                 680                 685

Leu Leu Glu Ala Cys Thr Phe Arg Arg Pro
        690                 695
```

NEAR-INFRARED DYE-BOUND TRANSFERRIN, AND CONTRAST AGENT FOR PHOTOACOUSTIC IMAGING, INCLUDING THE NEAR-INFRARED DYE-BOUND TRANSFERRIN

BACKGROUND OF THE INVENTION

Field of the Invention

The present invention relates to a near-infrared dye-bound transferrin, and a contrast agent for photoacoustic imaging, including the near-infrared dye-bound transferrin.

Description of the Related Art

A photoacoustic tomography (hereinafter, sometimes abbreviated as "PAT") apparatus is known as one apparatus for visualizing information in a living body. In measurement using the PAT apparatus, an image in which the substance distribution in an object to be measured is computed can be obtained by measuring the intensity and the time of generation of a photoacoustic signal emitted from a substance (optical absorber) that absorbs light in the object to be measured, in irradiation of the object to be measured with light.

For the optical absorber, any substance can be here used as long as the substance absorbs light and emits an acoustic wave in a living body. For example, a blood vessel or a malignant tumor in a human body can be adopted for the optical absorber. Besides, molecules of indocyanine green (hereinafter, sometimes abbreviated as "ICG") and the like can also be administered into a body and utilized as a contrast agent. ICG well absorbs light in the near-infrared wavelength region, the light having a small influence in irradiation of a human body therewith and having a high permeability to a living body, and therefore can be suitably used as a contrast agent (sometimes abbreviated as a "photoacoustic contrast agent") in the PAT apparatus. In the present description, ICG refers to a compound represented by a structure of the following formula.

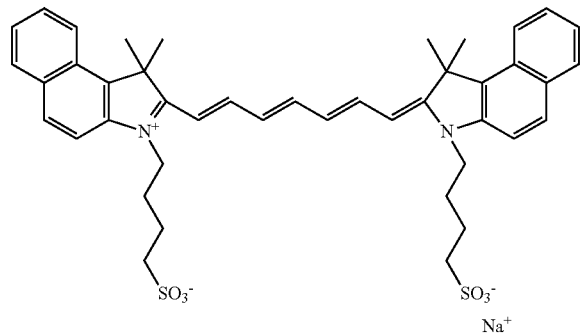

Herein, the counter ion may not be Na$^+$, and any counter ion such as H$^+$ or K$^-$ can be used.

It is known that, however, ICG has a very short half-life of about several minutes in blood.

NPL 1 (Photochemistry and Photobiology, 72, 234-241 (2000)) and NPL 2 (Molecular Imaging, 6, 85-95 (2007)) each disclose a compound in which an organic dye that absorbs light in the near-infrared wavelength region (hereinafter, sometimes abbreviated as "near-infrared dye") is bound to transferrin that is a serum protein (sometimes abbreviated as "TF"). The near-infrared dye herein means an organic dye that absorbs light in the near-infrared wavelength region. The light in the near-infrared wavelength region herein means light at wavelengths of 600 nm to 1300 nm.

In the transferrin, to which the near-infrared dye is bound, disclosed in NPL 1, the number of dyes to be immobilized is 2.4/molecule and such a dye is a hydrophilic near-infrared dye having a plurality of sulfonic acids in the molecule. The compound is shown to serve as a fluorescent contrast agent of a tumor. According to the animal experimental results described in the present Literature, the fluorescent contrast between a tumor and a normal tissue (hereinafter, sometimes abbreviated as "imaging contrast") is 1.9 at 24 hours after administration, and a further enhancement in the contrast is demanded for photoacoustic tumor imaging.

In the transferrin, to which an Alexa Fluor (registered trademark) 680 dye is bound, disclosed in NPL 2, the number of dyes to be immobilized is 2/molecule and such a dye is a hydrophilic near-infrared dye having a plurality of sulfonic acids in the molecule. As described later in Comparative Examples herein, the imaging contrast between a tumor and a normal tissue of the transferrin, to which the Alexa Fluor (registered trademark) 680 dye is bound, disclosed in is NPL 2, is 1.2 at 24 hours after administration, and a further enhancement in the contrast is demanded for photoacoustic tumor imaging.

Accordingly, a compound is demanded as a photoacoustic tumor contrast agent, which exhibits a high absorption coefficient in the near-infrared wavelength region, a high tumor accumulation property, a high tumor/blood ratio and a high imaging contrast.

The present invention has been made in view of such problems, and an object thereof is to provide a novel near-infrared dye-bound transferrin exhibiting a high absorption coefficient in the near-infrared wavelength region, a high tumor accumulation property, a high tumor/blood ratio and a high imaging contrast.

SUMMARY OF THE INVENTION

A contrast agent for photoacoustic imaging according to the present invention includes a near-infrared dye-bound transferrin in which transferrin and a near-infrared dye having a specified structure are bound.

Another contrast agent for photoacoustic imaging according to the present invention includes a compound represented by the following formula (I).

TF—(L—D)n         (I)

In the formula (I), TF represents transferrin, L represents a linker, D represents a near-infrared dye, n represents a number of 1 or more and L is optionally absent.

In the formula (I), D is represented by any of the following formulae (d1) to (d4).

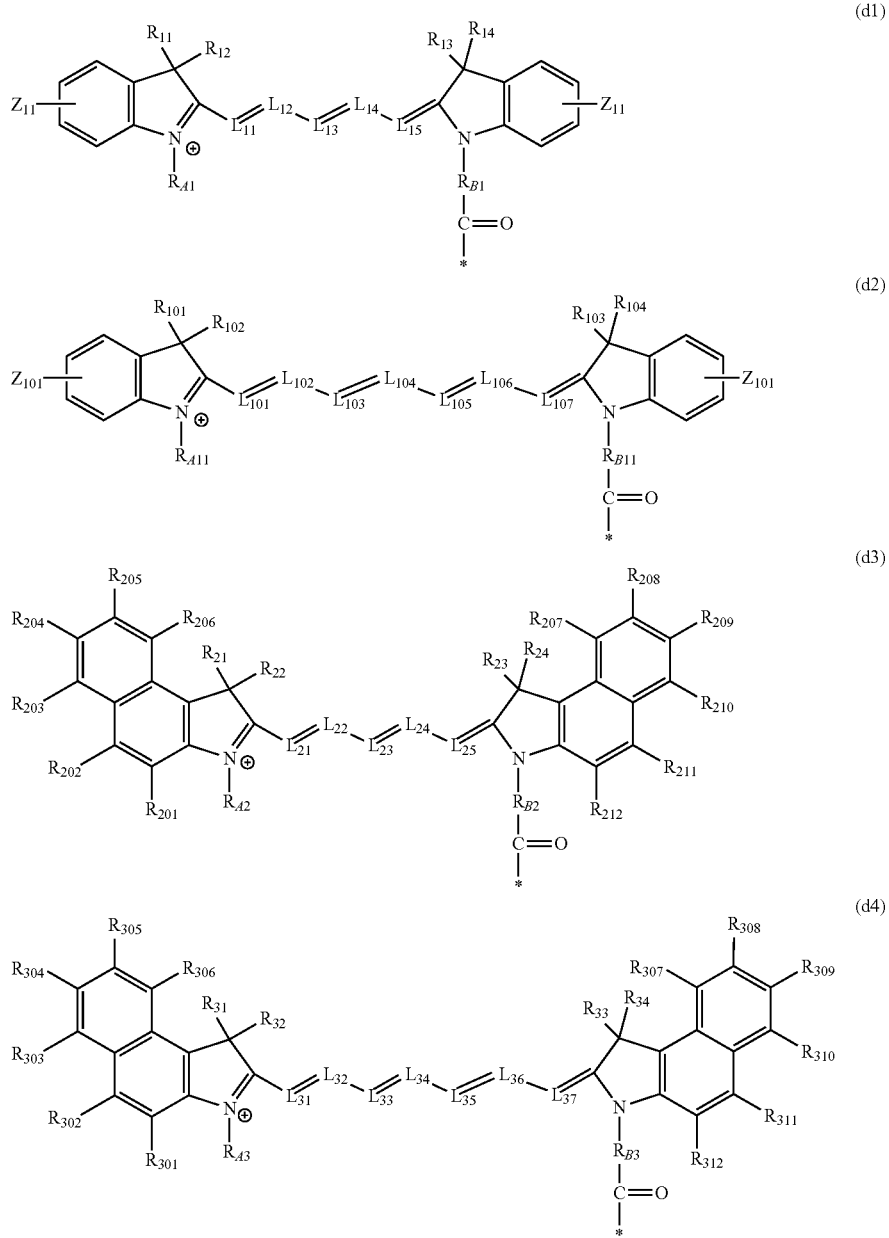

In the formula (d1), $L_{11}$, $L_{12}$, $L_{13}$, $L_{14}$ and $L_{15}$ may be each the same or different, and represent CH or $CR_{15}$, and $R_{15}$ represents a straight or branched alkyl group having 1 to 10 carbon atoms. $L_{11}$, $L_{12}$, $L_{13}$, $L_{14}$ and $L_{15}$ may be taken together to form a 4-membered ring to a 6-membered ring. $R_{11}$, $R_{12}$, $R_{13}$ and $R_{14}$ may be each the same or different, and represent a hydrogen atom, a straight or branched alkyl group having 1 to 10 carbon atoms, $-R_{D1}-SO_3-$, or $-R_{E1}-SO_3X_{11}$. $R_{D1}$ and $R_{E1}$ represent a straight or branched alkylene group having 1 to 10 carbon atoms. $X_{11}$ represents any of a hydrogen atom, a sodium atom, a potassium atom, or a cation derived from ammonia, triethylamine, lysine or arginine. $R_{A1}$ represents a straight or branched alkyl group having 1 to 10 carbon atoms, $-R_{C1}-SO_3^-$, $-R_{G1}-SO_3X_{15}$, or $-R_{F1}-CO_2X_{14}$. $X_{14}$ and $X_{15}$ represent any of a hydrogen atom, a sodium atom, a potassium atom, or a cation derived from ammonia, triethylamine, lysine or arginine. $R_{C1}$, $R_{F1}$ and $R_{G1}$ represent a straight or branched alkylene group having 1 to 10 carbon atoms. When $R_{A1}$ represents a straight or branched alkyl group having 1 to 10 carbon atoms, a halogen ion or an organic acid ion may be included as a counter ion. $R_{B1}$ represents a straight or branched alkylene group having 1 to 10 carbon atoms. $Z_{11}$ represents a hydrogen atom, or is taken together with an indole ring bound to $Z_{11}$ to form a cyclic aromatic ring including a benz[e]indole ring, a benz[f]indole ring or a benz[g]indole ring, and a hydrogen atom in the cyclic aromatic ring may be substituted with a straight or branched alkyl group having 1 to 10 carbon atoms, a straight or branched alkoxy group having 1 to 10 carbon atoms. * represents a binding bond bound to L, or to an amino group in the transferrin when the near-infrared dye-bound transferrin does not include L.

In the formula (d2), $L_{101}$, $L_{102}$, $L_{103}$, $L_{104}$, $L_{105}$, $L_{106}$ and $L_{107}$ may be each the same or different, and represent CH or $CR_{105}$, and $R_{105}$ represents a straight or branched alkyl group having 1 to 10 carbon atoms. $L_{101}$, $L_{102}$, $L_{103}$, $L_{104}$, $L_{105}$, $L_{106}$ and $L_{107}$ may be taken together to form a 4-membered ring to a 6-membered ring. $R_{101}$, $R_{102}$, $R_{103}$ and $R_{104}$ may be each the same or different, and represent a hydrogen atom, a straight or branched alkyl group having 1 to 10 carbon atoms, $-R_{D11}-SO_3^-$, or $-R_{E11}-SO_3X_{101}$. $R_{D11}$ and $R_{E11}$ represent a straight or branched alkylene group having 1 to 10 carbon atoms. $X_{101}$ represents any of a hydrogen atom, a sodium atom, a potassium atom, or a cation derived from ammonia, triethylamine, lysine or arginine. $R_{A11}$ represents a straight or branched alkyl group having 1 to 10 carbon atoms, $-R_{C11}-SO_3^-$, $-R_{G11}-SO_3X_{105}$, or $-R_{F1}-CO_2X_{104}$. $X_{104}$ and $X_{105}$ represent any of a hydrogen atom, a sodium atom, a potassium atom, or a cation derived from ammonia, triethylamine, lysine or arginine. $R_{C11}$, $R_{F11}$ and $R_{G11}$ represent a straight or branched alkylene group having 1 to 10 carbon atoms. When $R_{A11}$ represents a straight or branched alkyl group having 1 to 10 carbon atoms, a halogen ion or an organic acid ion may be included as a counter ion. $R_{B11}$ represents a straight or branched alkylene group having 1 to 10 carbon atoms. $Z_{101}$ represents a hydrogen atom, or is taken together with an indole ring bound to $Z_{101}$ to form a cyclic aromatic ring including a benz[e]indole ring, a benz[f]indole ring or a benz[g]indole ring, and a hydrogen atom in the cyclic aromatic ring may be substituted with a straight or branched alkyl group having 1 to 10 carbon atoms, a straight or branched alkoxy group having 1 to 10 carbon atoms. * represents a binding bond bound to L, or to an amino group in the transferrin when the near-infrared dye-bound transferrin does not include L.

In the formula (d3), $R_{201}$ to $R_{212}$ may be each the same or different, and represent a hydrogen atom, a straight or branched alkyl group having 1 to 10 carbon atoms, or $-SO_3X_{24}$. $X_{24}$ represents any of a hydrogen atom, a sodium atom, a potassium atom, or a cation derived from ammonia, triethylamine, lysine or arginine. $L_{21}$, $L_{22}$, $L_{23}$, $L_{24}$ and $L_{25}$ may be each the same or different, and represent CH or $CR_{25}$, and $R_{25}$ represents a straight or branched alkyl group having 1 to 10 carbon atoms. $L_{21}$, $L_{22}$, $L_{23}$, $L_{24}$ and $L_{25}$ may be taken together to form a 4-membered ring to a 6-membered ring. $R_{21}$, $R_{22}$, $R_{23}$ and $R_{24}$ may be each the same or different, and represent a hydrogen atom, a straight or branched alkyl group having 1 to 10 carbon atoms, $-R_{D2}-SO_3^-$, or $-R_{E2}-SO_3X_{21}$. $R_{D2}$ and $R_{E2}$ represent a straight or branched alkylene group having 1 to 10 carbon atoms. $X_{21}$ represents any of a hydrogen atom, a sodium atom, a potassium atom, or a cation derived from ammonia, triethylamine, lysine or arginine. $R_{42}$ represents a straight or branched alkyl group having 1 to 10 carbon atoms, $-R_{C2}-SO_3^-$, $-R_{G2}-SO_3X_{25}$, or $-R_{F2}-CO_2X_{26}$. $X_{25}$ and $X_{26}$ represent any of a hydrogen atom, a sodium atom, a potassium atom, or a cation derived from ammonia, triethylamine, lysine or arginine. $R_{C2}$, $R_{F2}$ and $R_{G2}$ represent a straight or branched alkylene group having 1 to 10 carbon atoms. When $R_{42}$ represents a straight or branched alkyl group having 1 to 10 carbon atoms, a halogen ion such as a chloride ion, a bromide ion or an iodide ion, or an organic acid ion such as an acetate ion, a tartrate ion or a succinate ion may be included as a counter ion. $R_{B2}$ represents a straight or branched alkylene group having 1 to 10 carbon atoms. * represents a binding bond bound to L, or to an amino group in the transferrin when the near-infrared dye-bound transferrin does not include L.

In the formula (d4), $R_{301}$ to $R_{312}$ may be each the same or different, and represent a hydrogen atom, a straight or branched alkyl group having 1 to 10 carbon atoms, or $-SO_3X_{34}$. $X_{34}$ represents any of a hydrogen atom, a sodium atom, a potassium atom, or a cation derived from ammonia, triethylamine, lysine or arginine. $L_{31}$, $L_{32}$, $L_{33}$, $L_{34}$, $L_{35}$, $L_{36}$ and $L_{37}$ may be each the same or different, and represent CH or $CR_{35}$, and $R_{35}$ represents a straight or branched alkyl group having 1 to 10 carbon atoms. $L_{31}$, $L_{32}$, $L_{33}$, $L_{34}$, $L_{35}$, $L_{36}$ and $L_{37}$ may be taken together to form a 4-membered ring to a 6-membered ring. $R_{31}$, $R_{32}$, $R_{33}$ and $R_{34}$ may be each the same or different, and represent a hydrogen atom, a straight or branched alkyl group having 1 to 10 carbon atoms, $-R_{D3}-SO_3^-$, or $-R_{E3}-SO_3X_{31}$. $R_{D3}$ and $R_{E3}$ represent a straight or branched alkylene group having 1 to 10 carbon atoms. $X_{31}$ represents any of a hydrogen atom, a sodium atom, a potassium atom, or a cation derived from ammonia, triethylamine, lysine or arginine. $R_{43}$ represents a straight or branched alkyl group having 1 to 10 carbon atoms, $-R_{C3}-SO_3^-$, $-R_{G3}-SO_3X_{35}$, or $-R_{F3}-CO_2X_{34}$. $X_{34}$ and $X_{35}$ represent any of a hydrogen atom, a sodium atom, a potassium atom, or a cation derived from ammonia, triethylamine, lysine or arginine. $R_{C3}$, $R_{F3}$ and $R_{G3}$ represent a straight or branched alkylene group having 1 to 10 carbon atoms. When $R_{43}$ represents a straight or branched alkyl group having 1 to 10 carbon atoms, a halogen ion such as a chloride ion, a bromide ion or an iodide ion, or an organic acid ion such as an acetate ion, a tartrate ion or a succinate ion may be included as a counter ion. $R_{B3}$ represents a straight or branched alkylene group having 1 to 10 carbon atoms. * represents a binding bond bound to L, or to an amino group in the transferrin when the near-infrared dye-bound transferrin does not include L.

In the formula (I), when L is included, L is represented by any of the following formulae (11) to (15).

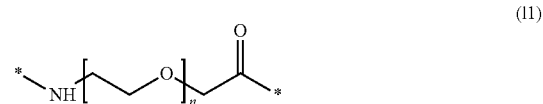

(11)

(12)

(13)

(14)

(15)

In the formulae (11) to (15), * represents binding to the transferrin or the near-infrared dye. In the formula (11), n is in the range from 1 to 500, and can be in the range from 1 to 120. In consideration of the binding ability to a transferrin receptor, n in the formula (11) can be in the range from 1 to 50.

Further features of the present invention will become apparent from the following description of exemplary embodiments with reference to the attached drawing.

BRIEF DESCRIPTION OF THE DRAWING

FIGURE is a diagram illustrating a fluorescent image of each cancer-bearing mouse at 24 hours after administration of each of iTF (2.0), iTF (4.8), iTF (7.0), iTF (8.3) and iTF (8.4) prepared in Examples of the present invention, and ICG in Comparative Example and Alexa Fluor 680-TF (2.0) in Comparative Example. Each arrow indicates a tumor site.

DESCRIPTION OF THE EMBODIMENTS

Preferred embodiments of the present invention will now be described in detail in accordance with the accompanying drawing.

A compound according to an embodiment of the present invention, and a contrast agent for photoacoustic imaging (hereinafter, sometimes abbreviated as "PAI") including the compound are described.

In the compound according to the present embodiment, transferrin and a near-infrared dye (organic dye having a specified structure) are covalently bound. That is, the present embodiment provides a near-infrared dye-bound transferrin. Herein, light in the near-infrared wavelength region means light at wavelengths of 600 nm to 1300 nm.

The near-infrared dye such as ICG, when administered in blood, adsorbs to protein in blood and is easily eliminated from the body. As a result, the near-infrared dye, even when singly administered in blood of a living body, is low in retentivity in blood and low in tumor accumulation property. Accordingly, when the near-infrared dye is singly used as a contrast agent for photoacoustic imaging, the photoacoustic signal intensity generated from a tumor is low.

On the other hand, in the compound according to the present embodiment, the near-infrared dye is covalently bound to the transferrin, and therefore the transferrin suppresses adsorption of protein in blood, to the near-infrared dye. Therefore, the compound according to the present embodiment, even when administered in blood of a living body, hardly adsorbs to protein in blood and is hardly eliminated from the body. Furthermore, the transferrin has the property of being incorporated in a cell via a transferrin receptor that is highly expressed in a cancer cell, and therefore the compound is enhanced in tumor accumulation property as compared with the near-infrared dye singly administered. From such a reason, the compound according to the present embodiment is higher in retentivity in blood and in tumor accumulation property than the near-infrared dye singly administered, and therefore is expected to exert the effect of increasing the photoacoustic signal intensity generated from a tumor. In addition, the compound of the present invention is incorporated in a cancer cell in a tumor tissue, and thus is also expected to be increased in tumor accumulation property in a short time after administration and maintained in the cell for a long period. Therefore, the effect of increasing the tumor/blood ratio is exerted. Therefore, the compound according to the present embodiment can serve as a contrast agent for PAI, in particular, a contrast agent for PAI of a tumor.

The near-infrared dye of the compound according to the present embodiment has a structure having no sulfonic acid group high in hydrophilicity on a benzene ring or a naphthyl ring bound to an indole ring. A structure high in hydrophobicity, such as a benzene ring and a naphthyl ring, contributes to hydrophobicity of the near-infrared dye. Surprisingly, hydrophobicity of the near-infrared dye largely contributes to hydrophobicity of the whole compound of the present embodiment. Accordingly, the compound according to the present embodiment, which comprises the near-infrared dye having no sulfonic acid group on the benzene ring or the naphthyl ring, exhibits moderate hydrophobicity, is circulated without being rapidly eliminated from blood, and is accumulated in a tumor due to the EPR effect during such circulation. It can be speculated that the hydrophobicity of the compound according to the present embodiment increase the interaction between the compound itself and a tumor cell in tumor site, resulting in enhancement of a tumor cell's incorporation of the compound. On the other hand, when the compound has a sulfonic acid group directly or via a linker on a nitrogen atom not bound to the transferrin, of two nitrogen atoms on the indole ring, the compound can impart a certain degree of hydrophilicity. The compound according to the present embodiment in blood is eliminated from a living body due to such hydrophilicity, and the concentration thereof in blood is reduced after a lapse of a certain time. That is, hydrophobicity and hydrophilicity of the compound according to the present embodiment can be balanced to thereby impart increased tumor accumulation property and tumor/blood ratio.

In the compound according to the present embodiment, at least one of the transferrin and at least one of the near-infrared dye may be covalently bound, or a plurality of the transferrins and a plurality of the near-infrared dyes may be covalently bound. When the compound includes the transferrin and a plurality of the near-infrared dyes, at least one of such near-infrared dyes may be covalently bound to the transferrin and other of such near-infrared dyes may be non-covalently bound thereto. Similarly, when the compound includes the near-infrared dye and a plurality of the transferrins, at least one of such transferrins may be covalently bound to the near-infrared dye, and other of such transferrins may be non-covalently bound thereto.

Specifically, the phrase "the transferrin and the near-infrared dye is covalently bound" mentioned in the present invention and the present specification means that a moiety (which can also be referred to as "radical") resulting from removal of a part (typically H or OH) of the transferrin and a moiety resulting from removal of a part (typically H or OH) of the near-infrared dye are covalently bound. The "compound" can be referred to as "molecule" from another perspective standpoint. The phrase "non-covalently bound" means binding by a bond other than a covalent bond, such as an ionic bond, a coordinate bond, a metallic bond, a hydrogen bond or an intermolecular force.

(Number of Dye(s) Labeled)

Herein, the average number of the near-infrared dye(s) covalently bound to one molecule of the transferrin refers to as "the number of the near-infrared dye(s) labeled". Hereinafter, the number of the near-infrared dye(s) labeled may be simply referred to as "the number of the dye(s) labeled". When the compound according to the present embodiment is formed of one molecule, the number n of the dye(s) labeled is an integer value. On the other hand, when a plurality of the compounds according to the present embodiment are aggregated to form a mixture, the number of the dye(s) labeled in the compounds is represented by the average of the numbers of the dye(s) labeled of the compounds forming the mixture. Accordingly, the number of the dye(s) labeled herein is not limited to an integer, but the number thereof actually labeled to the transferrin is an integer value. In the contrast agent for PAI, according to the present embodiment, the number of the dye(s) labeled is preferably 1 or more and preferably 9 or less, further preferably 2 or more and 8 or less, particularly preferably 4 or more and 7 or less. The reason therefore is because, when the number of the dye(s) labeled is in the above range, high tumor accumulation property and tumor/blood ratio are achieved.

Herein, the number of the dye(s) labeled is determined by determining the concentration of the near-infrared dye and the concentration of the transferrin, respectively, and calculating the ratio thereof (the concentration of the near-infrared dye/the concentration of the transferrin). The concentration of the near-infrared dye is calculated from the absorbance and the absorption coefficient at a specific adsorption wavelength of the dye. While 790 nm can be adopted as the specific adsorption wavelength in the case of use of, for example, ICG-Sulfo-OSu (compound represented by the following formula (d5-1)) as the near-infrared dye, other value can also be adopted as the specific adsorption wavelength. The concentration of the transferrin can be determined using the absorbance at 280 nm, at which absorption unique for protein is observed, and the absorption coefficient of the transferrin at such a wavelength, or can also be determined by a BCA method or the like. Herein, 92300 ($M^{-1} \times cm^{-1}$) described in NPL 1 is used as the molar absorption coefficient at 280 nm of the transferrin.

The contrast agent for PAI, according to the present embodiment, can include a compound represented by the following formula (I).

$$TF-(L-D)n \qquad (I)$$

In the formula (I), TF represents transferrin, L represents a linker, D represents the near-infrared dye and n represents the number of the dye(s) labeled. The number of the dye(s) labeled is a value calculated using the absorbance of each of the transferrin and the near-infrared dye, and the molar absorption coefficient thereof at such a wavelength. L is optionally absent.

In the formula (I), D is represented by any of the following formulae (d1) to (d4).

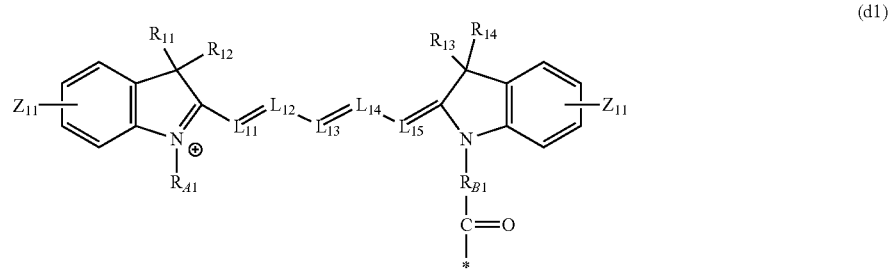
(d1)

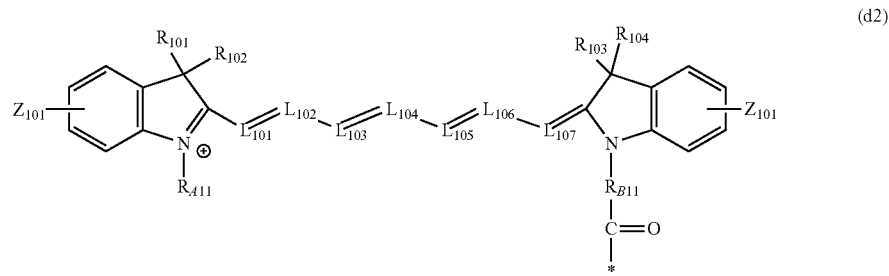
(d2)

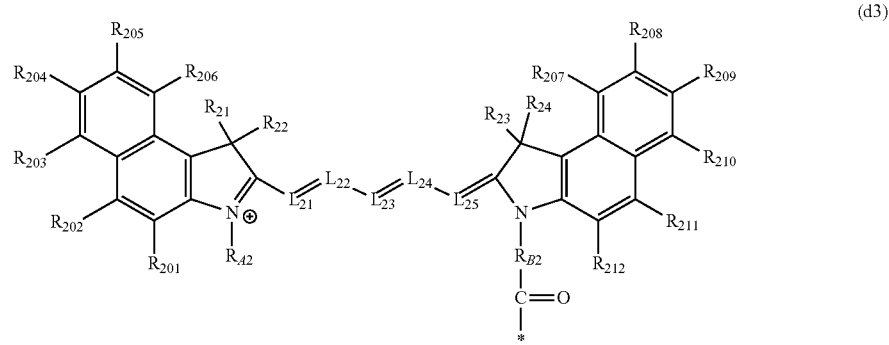
(d3)

(d4)

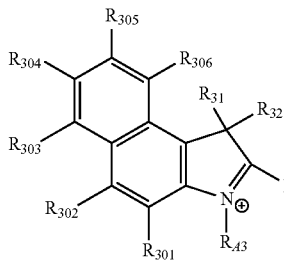
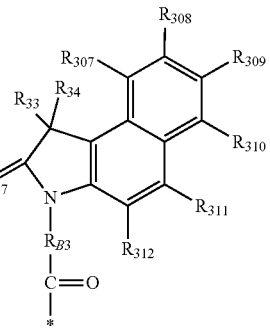

In the formula (d1), $L_{11}$, $L_{12}$, $L_{13}$, $L_{14}$ and $L_{15}$ may be each the same or different, and represent CH or $CR_{15}$, and $R_{15}$ represents a straight or branched alkyl group having 1 to 10 carbon atoms. $L_{11}$, $L_{12}$, $L_{13}$, $L_{14}$ and $L_{15}$ may be taken together to form a 4-membered ring to a 6-membered ring. $R_{11}$, $R_{12}$, $R_{13}$ and $R_{14}$ may be each the same or different, and represent a hydrogen atom, a straight or branched alkyl group having 1 to 10 carbon atoms, $-R_{D1}-SO_3^-$, or $-R_{E1}-SO_3X_{11}$. $R_{21}$ and $R_{E1}$ represent a straight or branched alkylene group having 1 to 10 carbon atoms. $X_{11}$ represents any of a hydrogen atom, a sodium atom, a potassium atom, or a cation derived from ammonia, triethylamine, lysine or arginine. $R_{A1}$ represents a straight or branched alkyl group having 1 to 10 carbon atoms, $-R_{C1}-SO_3^-$, $-R_{G1}-SO_3X_{15}$, or $-R_{F1}-CO_2X_{14}$. $X_{14}$ and $X_{15}$ represent any of a hydrogen atom, a sodium atom, a potassium atom, or a cation derived from ammonia, triethylamine, lysine or arginine. $R_{C1}$, $R_{F1}$ and $R_{G1}$ represent a straight or branched alkylene group having 1 to 10 carbon atoms. When $R_{A1}$ represents a straight or branched alkyl group having 1 to 10 carbon atoms, a halogen ion or an organic acid ion may be included as a counter ion. $R_{B1}$ represents a straight or branched alkylene group having 1 to 10 carbon atoms. $Z_{11}$ represents a hydrogen atom, or is taken together with an indole ring bound to $Z_{11}$ to form a cyclic aromatic ring including a benz[e]indole ring, a benz[f]indole ring or a benz[g]indole ring, and a hydrogen atom in the cyclic aromatic ring may be substituted with a straight or branched alkyl group having 1 to 10 carbon atoms, a straight or branched alkoxy group having 1 to 10 carbon atoms. * represents a binding bond bound to L, or to an amino group in the transferrin when the near-infrared dye-bound transferrin does not include L.

In the formula (d2), $L_{101}$, $L_{102}$, $L_{103}$, $L_{104}$, $L_{105}$, $L_{106}$ and $L_{107}$ may be each the same or different, and represent CH or $CR_{105}$, and $R_{105}$ represents a straight or branched alkyl group having 1 to 10 carbon atoms. $L_{101}$, $L_{102}$, $L_{103}$, $L_{104}$, $L_{105}$, $L_{106}$ and $L_{107}$ may be taken together to form a 4-membered ring to a 6-membered ring. $R_{101}$, $R_{102}$, $R_{103}$ and $R_{104}$ may be each the same or different, and represent a hydrogen atom, a straight or branched alkyl group having 1 to 10 carbon atoms, $-R_{D11}-SO_3^-$, or $-R_{E11}-SO_3X_{101}$. $R_{D11}$ and $R_{E11}$ represent a straight or branched alkylene group having 1 to 10 carbon atoms. $X_{101}$ represents any of a hydrogen atom, a sodium atom, a potassium atom, or a cation derived from ammonia, triethylamine, lysine or arginine. $R_{A11}$ represents a straight or branched alkyl group having 1 to 10 carbon atoms, $-R_{C11}-SO_3^-$, $-R_{G11}-SO_3X_{105}$, or $-R_{F1}-CO_2X_{104}$. $X_{104}$ and $X_{105}$ represent any of a hydrogen atom, a sodium atom, a potassium atom, or a cation derived from ammonia, triethylamine, lysine or arginine. $R_{C11}$, $R_{F11}$ and $R_{G11}$ represent a straight or branched alkylene group having 1 to 10 carbon atoms. When $R_{A11}$ represents a straight or branched alkyl group having 1 to 10 carbon atoms, a halogen ion or an organic acid ion may be included as a counter ion. $R_{B11}$ represents a straight or branched alkylene group having 1 to 10 carbon atoms. $Z_{101}$ represents a hydrogen atom, or is taken together with an indole ring bound to $Z_{101}$ to form a cyclic aromatic ring including a benz[e]indole ring, a benz[f]indole ring or a benz[g]indole ring, and a hydrogen atom in the cyclic aromatic ring may be substituted with a straight or branched alkyl group having 1 to 10 carbon atoms, a straight or branched alkoxy group having 1 to 10 carbon atoms. * represents a binding bond bound to L, or to an amino group in the transferrin when the near-infrared dye-bound transferrin does not include L.

In the formula (d3), $R_{201}$ to $R_{212}$ may be each the same or different, and represent a hydrogen atom, a straight or branched alkyl group having 1 to 10 carbon atoms, or $-SO_3X_{24}$. $X_{24}$ represents any of a hydrogen atom, a sodium atom, a potassium atom, or a cation derived from ammonia, triethylamine, lysine or arginine. $L_{21}$, $L_{22}$, $L_{23}$, $L_{24}$ and $L_{25}$ may be each the same or different, and represent CH or $CR_{25}$, and $R_{25}$ represents a straight or branched alkyl group having 1 to 10 carbon atoms. $L_{21}$, $L_{22}$, $L_{23}$, $L_{24}$ and $L_{25}$ may be taken together to form a 4-membered ring to a 6-membered ring. $R_{21}$, $R_{22}$, $R_{23}$ and $R_{24}$ may be each the same or different, and represent a hydrogen atom, a straight or branched alkyl group having 1 to 10 carbon atoms, $-R_{D2}-SO_3^-$, or $-R_{E2}-SO_3X_{21}$. $R_{D2}$ and $R_{E2}$ represent a straight or branched alkylene group having 1 to 10 carbon atoms. $X_{21}$ represents any of a hydrogen atom, a sodium atom, a potassium atom, or a cation derived from ammonia, triethylamine, lysine or arginine. $R_{A2}$ represents a straight or branched alkyl group having 1 to 10 carbon atoms, $-R_{C2}-SO_3^-$, $-R_{G2}-SO_3X_{25}$, or $-R_{F2}-CO_2X_{26}$. $X_{25}$ and $X_{26}$ represent any of a hydrogen atom, a sodium atom, a potassium atom, or a cation derived from ammonia, triethylamine, lysine or arginine. $R_{C2}$, $R_{F2}$ and $R_{G2}$ represent a straight or branched alkylene group having 1 to 10 carbon atoms. When $R_{A2}$ represents a straight or branched alkyl group having 1 to 10 carbon atoms, a halogen ion such as a chloride ion, a bromide ion or an iodide ion, or an organic acid ion such as an acetate ion, a tartrate ion or a succinate ion may be included as a counter ion. $R_{B2}$ represents a straight or branched alkylene group having 1 to 10 carbon atoms. * represents a binding bond bound to L, or to an amino group in the transferrin when the near-infrared dye-bound transferrin does not include L.

In the formula (d4), $R_{301}$ to $R_{312}$ may be each the same or different, and represent a hydrogen atom, a straight or branched alkyl group having 1 to 10 carbon atoms, or —SO$_3$X$_{34}$. X$_{34}$ represents any of a hydrogen atom, a sodium atom, a potassium atom, or a cation derived from ammonia, triethylamine, lysine or arginine. $L_{31}$, $L_{32}$, $L_{33}$, $L_{34}$, $L_{35}$, $L_{36}$ and $L_{37}$ may be each the same or different, and represent CH or CR$_{35}$, and $R_{35}$ represents a straight or branched alkyl group having 1 to 10 carbon atoms. $L_{31}$, $L_{32}$, $L_{33}$, $L_{34}$, $L_{35}$, $L_{36}$ and $L_{37}$ may be taken together to form a 4-membered ring to a 6-membered ring. $R_{31}$, $R_{32}$, $R_{33}$ and $R_{34}$ may be each the same or different, and represent a hydrogen atom, a straight or branched alkyl group having 1 to 10 carbon atoms, —R$_{D3}$—SO$_3^-$, or —R$_{E3}$—SO$_3$X$_{31}$. $R_{D3}$ and $R_{E3}$ represent a straight or branched alkylene group having 1 to 10 carbon atoms. X$_{31}$ represents any of a hydrogen atom, a sodium atom, a potassium atom, or a cation derived from ammonia, triethylamine, lysine or arginine. $R_{43}$ represents a straight or branched alkyl group having 1 to 10 carbon atoms, —R$_{C3}$—SO$_3^-$, —R$_{G3}$—SO$_3$X$_{35}$, or —R$_{F3}$—CO$_2$X$_{34}$. X$_{34}$ and X$_{35}$ represent any of a hydrogen atom, a sodium atom, a potassium atom, or a cation derived from ammonia, triethylamine, lysine or arginine. $R_{C3}$, $R_{F3}$ and $R_{G3}$ represent a straight or branched alkylene group having 1 to 10 carbon atoms. When $R_{43}$ represents a straight or branched alkyl group having 1 to 10 carbon atoms, a halogen ion such as a chloride ion, a bromide ion or an iodide ion, or an organic acid ion such as an acetate ion, a tartrate ion or a succinate ion may be included as a counter ion. $R_{B3}$ represents a straight or branched alkylene group having 1 to 10 carbon atoms. * represents a binding bond bound to L, or to an amino group in the transferrin when the near-infrared dye-bound transferrin does not include L.

In the respective formulae, $R_{41}$, $R_{411}$, $R_{42}$ and $R_{43}$ can each represent —R$_{C1}$—SO$_3^-$ or —R$_{G1}$—SO$_3$X$_{15}$. $R_{41}$, $R_{411}$, $R_{42}$ and $R_{43}$ can each have a sulfonic acid group to thereby impart a certain degree of hydrophilicity to the compound according to the present embodiment, and therefore the compound is easily eliminated from blood after a lapse of a certain time.

In the formula (I), L is represented by any of the following formulae (11) to (15).

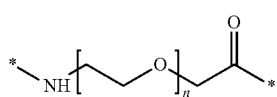

(11)

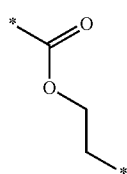

(12)

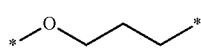

(13)

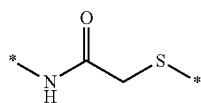

(14)

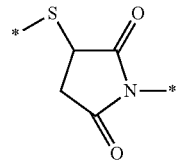

(15)

In the formulae (11) to (15), * indicates binding to the transferrin or the near-infrared dye. In the formula (11), n is in the range from 1 to 500, preferably in the range from 1 to 120. In consideration of the binding ability to the transferrin receptor, n in the formula (11) can be in the range from 1 to 50.

In the contrast agent for PAI, according to the present embodiment, D in the formula (I) can be represented by any of the following formulae (d5) to (d6).

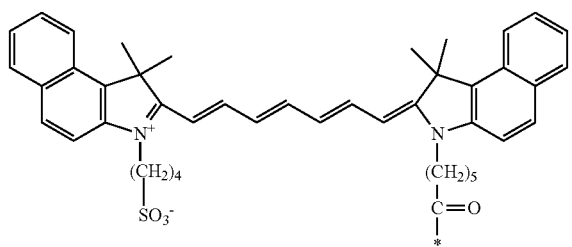

(d5)

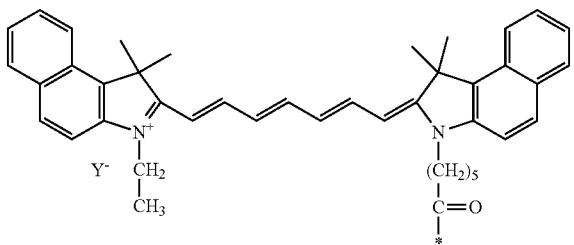

(d6)

In the formulae (d5) and (d6), * represents a binding bond bound to L, or to an amino group in the transferrin when the near-infrared dye-bound transferrin does not include L. In the formula (d6), Y$^-$ represents any of a halogen ion such as a chloride ion, a bromide ion or an iodide ion, or an organic acid ion such as an acetate ion, a tartrate ion or a succinate ion.

Herein, the compound according to the present embodiment can further have a capturing molecule. When the compound of the present embodiment can be used as a mixture of a plurality thereof aggregated, the average of n here is preferably 1 or more and the average of n is further preferably 4 or more and 7 or less.

In the compound of the present embodiment, the compound represented by the formula (I) can particularly have a structure represented by the following formula (I-1).

TF—(D)n        (I-1)

In the formula (I-1), TF represents transferrin, D represents a near-infrared dye represented by the following formula (d5) and n represents the number of the dye(s) labeled. The number of the dye(s) labeled is a value calculated using the absorbance of each of the transferrin and the near-infrared dye, and the molar absorption coefficient thereof at such a wavelength.

(d5)

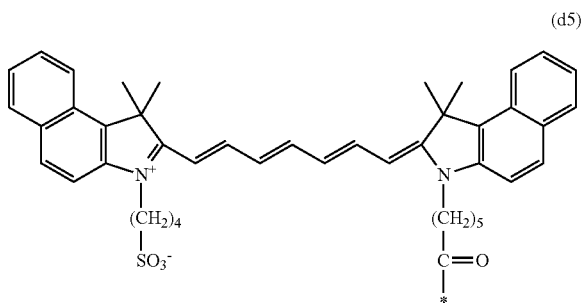

In the formula (I-1), TF represents a moiety resulting from removal of one or more amino groups for use in binding to the near-infrared dye, of the transferrin. In an example of the present embodiment, n in the formula (I-1) can be in the range of 4 or more and 7 or less.

The compound or the contrast agent for PAI, of the present embodiment, may also have a capturing molecule that is specifically bound to a target site. The compound of the present embodiment can be used as a mixture including a plurality of the compounds. The respective compounds included in the mixture may be different from each other in terms of n. The average of n of the compounds included in the mixture is preferably 1 or more, and the average of n is further preferably 4 or more and 7 or less.

(Transferrin)

The transferrin according to the present embodiment is a protein that is present in plasma and that has a molecular weight of about 80 kDa. The transferrin mainly has a role in transporting an iron ion. The transferrin according to the present embodiment may be derived from human serum or may be derived from animal serum other than human serum, such as bovine serum, rat serum or mouse serum, or may be a fragment thereof. The transferrin according to the present embodiment can be any of transferrin derived from human serum which is considered to be high in safety for a human body, and a variant and a fragment thereof. The transferrin according to the present embodiment may be an extract from human blood, may be a gene recombinant, or may be a product from *E. coli*, yeast, a cultured cell or the like.

An example of the sequence of human transferrin is shown. The transferrin in the example includes 698 amino acid residues and has a molecular weight of 76960.

```
                                              (SEQ ID NO: 1)
MRLAVGALLVCAVLGLCLAVPDKTVRWCAVSEHEATKCQSF

RDHMKSVIPSDGPSVACVKKASYLDCIRAIAANEADAVTLDAGLVYDAYL

APNNLKPVVAEFYGSKEDPQTFYYAVAVVKKDSGFQMNQLRGKKSCHTGL

GRSAGWNIPIGLLYCDLPEPRKPLEKAVANFFSGSCAPCADGTDFPQLCQ

LCPGCGCSTLNQYFGYSGAFKCLKDGAGDVAFVKHSTIFENLANKADRDQ

YELLCLDNTRKPVDEYKDCHLAQVPSHTVVARSIGGKEDLIWELLNQAQE

HFGKDKSKEFQLFSSPHGKDLLFKDSAHGFLKVPPRMDAKMYLGYEYVTA

IRNLREGTCPEAPTDECKPVKWCALSHHERLKCDEWSVNSVGKIECVSAE

TTEDCIAKIMNGEADAMSLDGGFVYIAGKCGLVPVLAENYNKSDNCEDTP

GAGYFAVAVVKKSASDLTWDNLKGKKSCHTAVGRTAGWNIPMGLLYNKIN

HCRFDEFFSEGCAPGSKKDSSLCKLCMGSGLNLCEPNNKEGYYGYTGAFR
```

-continued
```
CLVEKGDVAFVKHQTVPQNTGGKNPDPWAKNLNEKDYELLCLDGTRKPVE

EYANCHLARAPNHAVVTRKDKEACVHKILRQQQHLFGSNVTDCSGNFCLF

RSETKDLLFRDDTVCLAKLHDRNTYEKYLGEEYVKAVGNLRKCSTSSLLE

ACTFRRP
```

The transferrin according to the present embodiment has at least 95% homology to the above entire sequence or the partial sequence drawn from the entire sequence. The transferrin includes a plurality of lysine residues at a position where the near-infrared dye can be covalently bound. One example of a chemical bond formed by the transferrin and the near-infrared dye includes an amide bond formed by an amino group of a lysine residue of the transferrin and a carboxyl group of the near-infrared dye.

(Near-Infrared Dye)

In the present embodiment, the near-infrared dye is not particularly limited as long as the near-infrared dye is an organic dye that absorbs light in the near-infrared wavelength region to generate an acoustic wave. Examples of the near-infrared dye in the present embodiment can include an azine type dye, an acridine type dye, a triphenylmethane type dye, a xanthene type dye, a porphyrin type dye, a cyanine type dye, a phthalocyanine type dye, a styryl type dye, a pyrylium type dye, an azo type dye, a quinone type dye, a tetracycline type dye, a flavone type dye, a polyene type dye, a BODIPY (registered trademark) type dye and an indigoid type dye. Examples of the cyanine type dye include Indocyanine Green (ICG) and a derivative thereof.

In the present embodiment, the near-infrared dye for preparing the compound of the present invention has a functional group, which can be covalently bound to the transferrin, in the dye. Examples include an amino group, a thiol group, a carboxyl group, a hydroxyl group or an N-hydroxysuccinimide group. One example of the near-infrared dye for preparing the compound of the present invention, which can be used, is a dye represented by the following formula (d5-1). When the dye is used, an N-hydroxysuccinimide group of the dye forms an amide bond with a nucleophilic group of the transferrin, for example, an amino group of a lysine residue, and therefore the dye is fixed to the transferrin.

(d5-1)

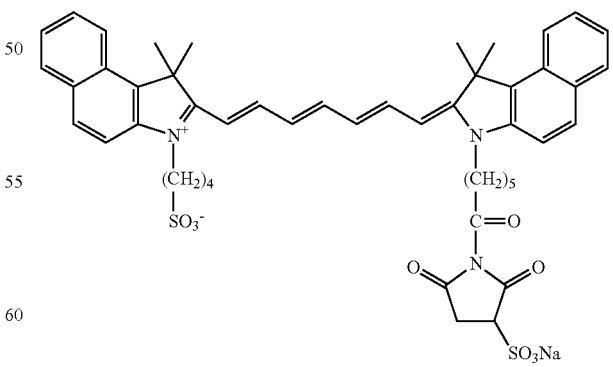

(Method for Preparing Compound)

In the present embodiment, the transferrin and the near-infrared dye can be covalently bound by a known coupling reaction via an amino group, a thiol group, a carboxyl group or a hydroxyl group. In particular, the transferrin and the near-infrared dye can be bound via an amino group of the transferrin. A plurality of such amino groups are present in the transferrin, and in particular, a primary amino group of a lysine residue is nucleophilically reacted with an N-hydroxysuccinimide group of the near-infrared dye in a weak alkaline pH region in an efficient and selective manner. The near-infrared dye bound to the transferrin by the reaction can be washed and purified by a known protein purification method such as an ultrafiltration method, a size exclusion column chromatography method or dialysis.

(Linker)

In the contrast agent for PAI, according to the present embodiment, the transferrin and the near-infrared dye may be bound by directing binding the amino group, thiol group, carboxyl group or hydroxyl group present on the transferrin surface and a derivative of the near-infrared dye, or may be bound by binding the transferrin and the near-infrared dye via various linkers (also referred to as "crosslinking agent" or "crosslinker").

In the present embodiment, a linker represented by any of the following formulae (11) to (15) can be used.

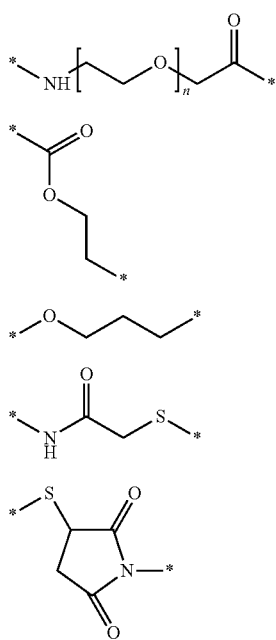

In the formulae (11) to (15), * represents binding to the transferrin or the near-infrared dye, and any of two *(s) may be bound to the transferrin or the infrared dye.

(Dispersion Medium)

The contrast agent for PAI, according to the present embodiment, may include a dispersion medium besides the compound. Herein, PAI means a concept including photoacoustic tomography (tomographic method). Examples of the dispersion medium include saline, distilled water for injection, phosphate buffered saline and an aqueous glucose solution. The contrast agent for PAI according to the present embodiment may, if necessary, have a pharmacologically acceptable additive, for example, a surfactant.

The contrast agent for PAI according to the present embodiment may be dispersed in the dispersion medium in advance, or may be in the form of a kit and may be dispersed in the dispersion medium for use before administration into a living body.

The contrast agent for PAI according to the present embodiment can be more accumulated in a tumor site than a normal site in a living body in administration to the living body by means of the Enhanced Permeability and Retention (EPR) effect. As a result, when a particle is administered to the living body and thereafter the living body is irradiated with light and an acoustic wave from the living body is detected, an acoustic wave emitted from a tumor site can be enlarged as compared to an acoustic wave emitted from a normal site. Accordingly, the contrast agent for PAI according to the present embodiment can be used for imaging a tumor. The contrast agent for PAI, according to the present embodiment, is a compound in which the transferrin serves as a matrix, and has the property of being incorporated in a cancer cell via a transferrin receptor expressed in a cancer cell. Accordingly, while tumor accumulation property is expected to be maintained for a long period by not only the EPR effect but also incorporation of the compound of the present invention in a cell, the concentration in blood is decreased over time and, as a result, a high tumor/blood ratio can be expected to be exhibited. Transferrin is less likely to remain in blood after administration because the half-life of transferrin is about as half as that of serum albumin. Therefore, transferring is preferable as a contrast agent and is expected to contribute to a high tumor/blood ratio.

(Capturing Molecule)

The compound or the contrast agent for PAI, of the present embodiment, may have a capturing molecule that is specifically bound to a target site. The capturing molecule means a substance that is specifically bound to a target site such as a tumor, a substance that is specifically bound to a substance present around a target site, or the like, and can be arbitrarily selected from a biomolecule and a chemical substance such as a medicine. Specific examples include a protein, an antibody, an antibody fragment, an enzyme, bioactive peptide, glycopeptide, polypeptide, peptide, a sugar chain, a lipid and a molecule-recognizing compound. Such substances can be used singly or can be used in combinations of a plurality thereof. The compound to which the capturing molecule is chemically bound can be used to thereby perform specific detection of a target site, and tracking of dynamic, localization, drug efficacy, metabolism and the like of a target substance. In the present embodiment, the protein refers to one in which 90 or more natural or unnatural amino acids are linked by an amide bond. In the present embodiment, the polypeptide refers to one in which 30 or more and less than 90 natural or unnatural amino acids are linked by an amide bond. In the present embodiment, the peptide refers to one in which less than 30 natural or unnatural amino acids are linked by an amide bond. In the present embodiment, the protein, the polypeptide and the peptide are classified depending on the number of amino acids linked, regardless of the presence of various modifications. In the present embodiment, the capturing molecule can be the protein, the polypeptide or the peptide.

(Additive)

The contrast agent for photoacoustic imaging according to the present embodiment may also include an additive for use in freeze-drying. One example of the additive includes glucose, lactose, mannitol, polyethylene glycol, glycine, sodium chloride and sodium hydrogen phosphate. The additive may be used singly or in combinations of a plurality thereof.

(Photoacoustic Imaging Method)

The method for detecting the contrast agent for PAI according to the present embodiment, administered into a living body, by use of a photoacoustic imaging apparatus is described. A method for detecting the contrast agent for PAI according to the present embodiment includes the following steps (a) and (b). Herein, the photoacoustic imaging method according to the present embodiment may also include step(s) other than the following steps:

(a) a step of irradiating a specimen, to which the contrast agent for PAI is administered, with light in a wavelength region of 600 nm to 1300 nm; and
(b) a step of detecting an acoustic wave emitted from the contrast agent present in the specimen.

The photoacoustic imaging method according to the present embodiment may include a step of reconstructing a spatial photoacoustic signal intensity distribution from the wavelength, phase, time information and the like of the acoustic wave obtained in step (b) above. Herein, three-dimensional image reconstruction can be conducted based on the wavelength, phase and time information of the photoacoustic signal obtained in step (b) above. Data obtained by the image reconstruction may take any form as long as the position information of the intensity distribution of the photoacoustic signal can be grasped from the data. For example, a form may be taken in which the photoacoustic signal intensity is exhibited on a three-dimensional space, or a form may be taken in which the photoacoustic signal intensity is exhibited on a two-dimensional plane. In addition, the following form can also be taken: information on the same observation object is acquired by a different imaging method and the positional correspondence relationship between such pieces of information and the photoacoustic intensity distribution is acquired.

In step (a) above, the specimen to which the contrast agent for PAI according to the present embodiment is administered by a method such as oral administration or injection can be used.

In step (a) above, an apparatus that emits light with which the specimen is irradiated, and an apparatus that detects the photoacoustic signal emitted from the contrast agent for PAI according to the present embodiment are not particularly limited.

A light source for irradiation of the specimen with light in step (a) above is not limited as long as the light source can irradiate the specimen with laser pulse light having at least one wavelength selected from the range from 600 nm to 1300 nm. Examples of the apparatus for irradiating the specimen with laser pulse light include a titanium sapphire laser (LT-2211-PC, manufactured by Lotis TII), an OPO laser (LT-2214 OPO, manufactured by Lotis TII) and an alexandrite laser.

The photoacoustic imaging apparatus is not particularly restricted and various apparatuses can be used. For example, such detection can be conducted using a commercially available photoacoustic imaging apparatus (Nexus128, manufactured by Endra Inc.).

The imaging method using the contrast agent for PAI according to the present embodiment can image an objective site such as a tumor or a blood vessel through steps (a) and (b) above.

EXAMPLES

Hereinafter, the present invention is described in more detail with reference to Examples, but the present invention is not limited to such Examples, and materials, compositional conditions, reaction conditions and the like can be freely changed as long as a dye-modified transferrin having the same function and effect is obtained.

(Calculation of Number of Dye(s) Labeled)

In Examples of the present invention, the number of the dye(s) labeled to the transferrin was calculated by measurement of the absorbance of the compound. In other words, a solution of the compound in water was prepared, and the absorbance of each of the dye and the transferrin was measured to thereby determine the concentration of each of the dye and the transferrin, and the concentration of the dye was divided by the concentration of the transferrin to thereby determine the number of the dye(s) labeled.

Specifically, in the case of a compound prepared using ICG-Sulfo-OSu (compound represented by the following formula (d5-1)), the absorbance at 790 nm of the compound diluted with 5% sodium dodecyl sulfate (hereinafter, abbreviated as "SDS") in a solution of the compound in water was measured. The absorbance was from ICG. The concentration of ICG was determined by calculating the concentration of the dye by use of an absorption coefficient at 790 nm of 120000 ($M^{-1} \times cm^{-1}$) calculated from the calibration curve in SDS created in advance. The concentration of the transferrin was calculated by measuring the absorbance at 280 nm of the transferrin in phosphate buffered saline (sometimes abbreviated as "PBS"), and using the absorbance and a molar absorption coefficient of 92300 ($M^{-1} \times cm^{-1}$) of the transferrin. The number of the dye(s) labeled was determined by dividing the concentration of the dye by the concentration of the transferrin. Herein, with respect to the absorbance at 280 nm of the transferrin, the value obtained by multiplying the absorbance at 790 nm of ICG by 0.4 was subtracted from the absorbance at 280 nm measured, to thereby correct the contribution of the absorbance at 280 nm of ICG-Sulfo-OSu to the absorbance at 280 nm of the transferrin.

Example 1: Preparation of Near-Infrared Dye-Bound Transferrin

The compound in the present Example was obtained by covalently binding the near-infrared dye to an amino group on the transferrin surface. Hereinafter, one example of the preparation method is shown.

First, 10 mg of transferrin (transferrin human, T3309, produced by Sigma-Aldrich Japan K.K.) was dissolved in 1 mL of carbonate buffer (pH: 9.0) to provide a transferrin solution. One mg of a near-infrared dye represented by the following formula (d5-1) (ICG-Sulfo-OSu, I254, produced by Dojindo Laboratories) was dissolved in 0.1 mL of dimethyl sulfoxide (hereinafter, sometimes abbreviated as "DMSO"). The respective solutions were mixed in a plastic tube, and rotated and stirred at room temperature for 3 hours. The resulting reaction solution was filtered by a 0.22-μm syringe filter, and the filtrate was recovered. Sephacryl Gel S-400 was added to the solution recovered, and the resultant was rotated and stirred at room temperature for 1 hour. Next, the gel-containing solution was centrifuged, and a supernatant portion was recovered while the gel present at the bottom of the plastic tube was not fractionated. Finally, a green solution recovered was filtered by a 0.22-μm syringe filter to thereby provide a compound (hereinafter, sometimes abbreviated as "iTF") according to the present invention, in which the near-infrared dye and the transferrin were covalently bound.

The numbers of the dye(s) labeled of respective compounds obtained by changing the feeding molar ratio (near-infrared dye:transferrin) in the reaction are shown in Table 1. It was found from Table 1 that the feeding molar ratio of the near-infrared dye to the transferrin was changed to thereby change the number of the dye(s) labeled in any range. Hereinafter, such compounds having numbers of the dye(s) labeled of 2.0, 4.8, 7.0, 8.3 and 8.4 are abbreviated as "iTF (2.0)", "iTF (4.8)", "iTF (7.0)", "iTF (8.3)" and "iTF (8.4)", respectively.

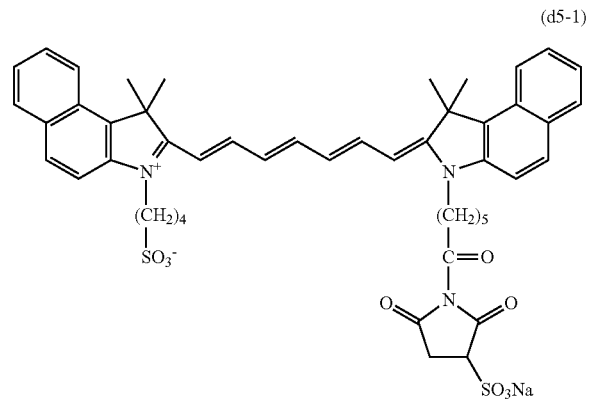

(d5-1)

TABLE 1

| Sample name | Feeding molar ratio (near-infrared dye:transferrin) | Number of dye(s) labeled |
| --- | --- | --- |
| iTF (2.0) | 3.0 | 2.0 |
| iTF (4.8) | 8.0 | 4.8 |
| iTF (7.0) | 15.0 | 7.0 |
| iTF (8.3) | 25.0 | 8.3 |
| iTF (8.4) | 50.0 | 8.4 |

Example 2: Measurement of Photoacoustic Signal

The photoacoustic signals of a solution of each of iTF (2.0), iTF (4.8), iTF (7.0), iTF (8.3) and iTF (8.4) obtained in Example 1 in water, and a solution of ICG represented by the following formula, in Comparative Example, in water were measured.

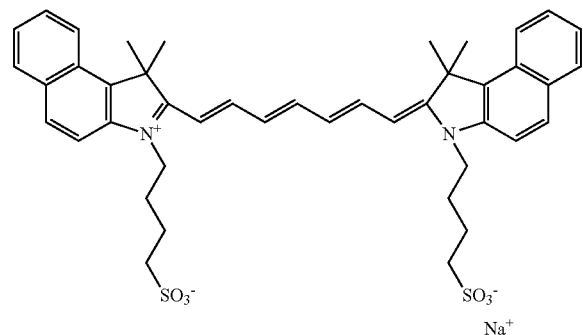

The photoacoustic signal was measured by irradiating an aqueous sample solution with pulse laser light, detecting the photoacoustic signal from the sample by using a piezoelectric element, amplifying the signal by a high-speed preamplifier, and then acquiring the signal by a digital oscilloscope. Specific conditions were as follows. A titanium sapphire laser (LT-2211-PC, manufactured by Lotis TII) was used as a light source. The laser wavelength was 790 nm. The energy density was from about 10 to 20 mJ/cm$^2$, the pulse width was about 20 nanoseconds, and the pulse repetition frequency was 10 Hz. As the piezoelectric element for detecting the photoacoustic signal, a non-convergence type ultrasonic transducer (V303, manufactured by Panametrics-NDT) having an element diameter of 1.27 cm and a central band of 1 MHz was used. The measurement vessel was a polystyrene cuvette having an optical path length of 0.1 cm and a sample volume of about 200 μl. The measurement vessel and the piezoelectric element were immersed in a glass vessel filled with water and the distance therebetween was set to be 2.5 cm. As the high-speed preamplifier for amplifying the photoacoustic signal intensity, an ultrasonic preamplifier (Model 5682, manufactured by Olympus Corp.) having an amplification degree of +30 dB was used. The signal amplified was input to a digital oscilloscope (DPO4104, manufactured by Tektronix). The polystyrene cuvette was irradiated with pulse laser light from the outside of the glass vessel. A portion of scattering light generated here was detected by a photodiode, and input as a trigger signal to the digital oscilloscope. The digital oscilloscope was set to a 32 run-averaging display mode to measure the photoacoustic signal intensity on average of 32 laser pulse irradiations.

The photoacoustic signal intensities of the solution of each of iTF (2.0), iTF (4.8), iTF (7.0), iTF (8.3) and iTF (8.4) according to Examples of the present invention in water, and the solution of ICG in Comparative Example in water were shown in Table 2. In Table 2, relative intensities under assumption of the photoacoustic signal intensity of ICG to 1 were shown. As is clear from Table 2, it was found that a large number of the near-infrared dyes could be bound to each transferrin and therefore the photoacoustic signal from each transferrin was increased in the range from 1.8 times to even 10.8 times the photoacoustic signal from ICG. From the result, it has been indicated that iTF(s) of the present invention are each a contrast agent for photoacoustic imaging, which can perform photoacoustic imaging at a high sensitivity.

TABLE 2

| Sample name | PA signal intensity (ICG = 1) |
| --- | --- |
| ICG | 1.0 |
| iTF (2.0) | 1.8 |
| iTF (4.8) | 5.0 |
| iTF (7.0) | 8.8 |
| iTF (8.3) | 10.4 |
| iTF (8.4) | 10.8 |

Example 3: Evaluation of Incorporation Ability in Cancer Cell

The incorporation ability of each of iTF (2.0), iTF (4.8), iTF (7.0), iTF (8.3) and iTF (8.4) obtained in Example 1, and Alexa Fluor (registered trademark) 680 near-infrared dye-bound transferrin (Transferrin From Human Serum, Alexa Fluor (registered trademark) 680 Conjugate, produced by Life Technologies, Product No. T35357, the number of the dye(s) labeled: 2.0) in Comparative Example in a cancer cell was measured. Hereinafter, Alexa Fluor (registered trademark) 680 near-infrared dye-bound transferrin is abbreviated as "Alexa Fluor 680-TF (2.0)".

The measurement method of the incorporation ability was performed as follows. First, colon 26 mouse colon cancer cells (RIKEN) were seeded into a 24-well plastic plate and cultured. On the next day, the culture medium was removed and exchanged with a fresh culture medium, and thereafter each of iTF (2.0), iTF (4.8), iTF (7.0), iTF (8.3) and iTF (8.4), and Alexa Fluor 680-TF (2.0) was added so that the concentration of each dye was 10 µM. The resultant was incubated under conditions of 37° C. and 5% $CO_2$ for 24 hours. Next, the culture medium was removed and the cells were washed with PBS twice, and thereafter the cells were peeled by Trypsin-EDTA and recovered. The number of the cells was counted and thereafter the cells were lysed using a 1% Triton X100 solution. After DMSO was added to the lysate of the cells, the ICG fluorescence intensity of the lysate was measured to thereby measure the amount of ICG incorporated in the cells.

The relative value of the amount of each dye incorporated is shown in Table 3. Each of iTF (2.0), iTF (4.8), iTF (7.0), iTF (8.3) and iTF (8.4) of the present invention exhibited an incorporation ability about 20 to 60 times higher than the incorporation ability of Alexa Fluor 680-TF (2.0) in Comparative Example. In comparison of Alexa Fluor 680-TF (2.0) and iTF (2.0) of the present invention which were close in terms of the number of the dye(s) labeled, iTF (2.0) of the present invention exhibited an enhanced incorporation ability even 60 times. Such a difference is considered to be due to the influence of hydrophilicity and hydrophobicity of the dye. While the structure of Alexa Fluor 680 is not published, the structure is considered to have high hydrophilicity imparted by introduction of sulfonic acid. On the other hand, the dye backbone of iTF (2.0) includes no sulfonic acid and exhibits hydrophobicity. Accordingly, it was considered that the transferrin was labeled by the dye and thus exhibited hydrophobicity and was promoted in adsorption to the cells, resulting in an increase in the incorporation ability in the cells. The compound was shown to be a very useful compound as a tumor contrast agent based on incorporation in a cancer cell.

TABLE 3

| Sample name | Relative value of amount of dye incorporated |
| --- | --- |
| iTF (2.0) | 60.3 |
| iTF (4.8) | 27.7 |
| iTF (7.0) | 21.2 |
| iTF (8.3) | 24.1 |
| iTF (8.4) | 30.1 |
| AlexaFluor680-TF (2.0) | 1.0 |

Example 4: Evaluation of Tumor-Imaging Contrast by Fluorescence Imaging

The tumor-imaging contrast of each of iTF (2.0), iTF (4.8), iTF (7.0), iTF (8.3) and iTF (8.4) obtained in Example 1, and ICG and Alexa Fluor 680-TF (2.0) in Comparative Examples was evaluated by fluorescence imaging by use of a cancer-bearing mouse. In the fluorescence imaging experiment, a female outbred BALB/c Slc-nu/nu mouse (6-week-old at the time of purchase) (Japan SLC, Inc.) was used. For one week before the mouse was allowed to bear a cancer, normal diet and bed were used to habituate the mouse to an environment where the diet and drinking water were available ad libitum. Before about one week of the imaging experiment, $1\times10^6$ colon 26 mouse colon cancer cells (RIKEN) were subcutaneously injected into the femur area of the mouse to thereby prepare a cancer-bearing model mouse.

With respect to the whole-body fluorescence image of the cancer-bearing mouse to which each of iTF (2.0), iTF (4.8), iTF (7.0), iTF (8.3), iTF (8.4), ICG and Alexa Fluor 680-TF (2.0) was administered, the bright field image and the fluorescence image of the mouse after 24 hours of the administration were acquired using IVIS (registered trademark) Imaging System 200 Series (XENOGEN). The amounts of iTF (2.0), iTF (4.8), iTF (7.0), iTF (8.3) and iTF (8.4), and ICG to be administered were each 10 nmol per mouse as the amount of the dye, the amount of Alexa Fluor 680-TF (2.0) to be administered was 31 nmol per mouse as the amount of the dye, and such dyes were each injected as 100 µL of a PBS solution to the tail vein of each mouse.

FIGURE illustrates a representative example of a fluorescence image of each mouse at 24 hours after administration of each of iTF (2.0), iTF (4.8), iTF (7.0), iTF (8.3), iTF (8.4), ICG and Alexa Fluor 680-TF (2.0). In FIGURE, each arrow indicates the position of a tumor in the femur area. As is clear from FIGURE, no fluorescent signal was observed with respect to ICG in Comparative Example at all, but the fluorescent signal from the tumor site was observed with respect to each of iTF (2.0), iTF (4.8), iTF (7.0), iTF (8.3) and iTF (8.4) of the present invention. It has been found from the results that each of iTF (2.0), iTF (4.8), iTF (7.0), iTF (8.3) and iTF (8.4) of the present invention can be accumulated in the tumor.

In order to evaluate the tumor-imaging contrast, the fluorescence intensity of a tumor site (measured area: 0.5× 0.5 cm) and the fluorescence intensity (selected as a normal site, measured area: 0.5×0.5 cm) of the base of a leg were quantified from the fluorescence imaging data illustrated in FIGURE. The ratio of the intensities, namely, the value obtained by dividing the value of the fluorescence intensity of a tumor site by the value of the fluorescence intensity of a normal site, was expressed by a numeral value as an imaging contrast. The imaging contrast is a parameter showing the tumor-imaging ability of each compound, and a higher imaging contrast results in a more effective contrast agent of a tumor. Table 4 shows the imaging contrast of each compound. The imaging contrast of each of iTF (2.0), iTF (4.8), iTF (7.0), iTF (8.3) and iTF (8.4) of the present invention was 2.3 or more, and was higher than the imaging contrast of each of ICG and Alexa Fluor 680-TF (2.0) in Comparative Examples. From the result, the near-infrared dye-bound transferrins according to Examples of the present invention were shown to be excellent in tumor-imaging ability. A larger imaging contrast of the compound of the present invention than the imaging contrast of Alexa Fluor 680-TF (2.0) is considered to be due to the difference in tumor accumulation property, as described later. The number of the dye(s) labeled at which the highest imaging contrast was achieved was 4.8. On the other hand, when the number of the dye(s) labeled exceeded 8, a tendency of the imaging contrast to be reduced was observed.

TABLE 4

| Sample name | Imaging contrast |
| --- | --- |
| ICG | 1.2 |
| iTF (2.0) | 3.3 |
| iTF (4.8) | 4.1 |
| iTF (7.0) | 3.4 |
| iTF (8.3) | 3.3 |
| iTF (8.4) | 2.3 |
| AlexaFluor680-TF (2.0) | 1.2 |

Example 5: Evaluations of Tumor Accumulation Property and Residual Rate in Blood of Compound The amount of the dye in a tumor and the amount of the dye in blood with respect to each mouse in the tumor-imaging experiment performed in Example 4 were quantitatively determined to thereby evaluate the tumor accumulation property and the residual rate in blood of each compound.

The tumor accumulation property was expressed as the rate of dye transfer (% ID/g) to a tumor relative to the amount of the dye to be administered per gram of the tumor. First, the mouse was euthanized by a carbon dioxide gas after 24 hours of administration, and thereafter the tumor was surgically resected. The tumor was transferred to a plastic tube, an aqueous 1% Triton-X100 solution was added at 1.25 times the weight of the tumor, and the tumor was crushed using a plastic pestle. Next, DMSO was added at 20.25 times the weight of the tumor tissue. The fluorescence intensity of the solution of the tumor crushed, treated as described above, was measured in the plastic tube using IVIS (registered trademark) Imaging System 200 Series (XENOGEN) to thereby measure the amount of the dye in the tumor.

The residual rate in blood was expressed as the rate of dye transfer (% ID/g) to blood relative to the amount of the dye to be administered per gram of blood (1 mL when the specific gravity was assumed to be 1). A blood sample was taken from the tail vein of the mouse after 24 hours of administration, and the blood sample, 1% Triton (registered trademark) X-100 and DMSO were mixed in the plastic tube in a ratio of 2:9:9. The fluorescence intensity of the blood solution treated as described above was measured in the plastic tube using IVIS (registered trademark) Imaging System 200 Series (manufactured by XENOGEN) to thereby measure the amount of the dye in blood.

The tumor/blood ratio was calculated by the above measurements. The ratio corresponds to the ratio of the tumor accumulation property to the residual rate in blood, and a higher ratio means a higher tumor-imaging ability.

The results are shown in Table 5. The tumor accumulation property of each of iTF (2.0), iTF (4.8), iTF (7.0), iTF (8.3) and iTF (8.4) of the present invention was 0.8 to 7.1% ID/g, and a highest tumor accumulation property of 7.1% ID/g was exhibited in iTF (4.8). ICG in Comparative Example had no tumor accumulation property and the rate of tumor accumulation was zero. The rate of tumor accumulation of Alexa Fluor 680-TF (2.0) in Comparative Example was 0.6% ID/g. A higher rate of tumor accumulation of each of the compounds of the present invention than the rate of tumor accumulation of Alexa Fluor 680-TF (2.0) is considered to be due to the influence of hydrophilicity and hydrophobicity of the dye. While the structure of Alexa Fluor 680 is not published, the structure is considered to have high hydrophilicity imparted by introduction of sulfonic acid. On the other hand, the dye backbone of iTF of the present invention includes no sulfonic acid and exhibits hydrophobicity. Accordingly, it was considered that the transferrin was labeled by the dye and thus exhibited hydrophobicity and was increased in the incorporation ability in the cells, resulting in an increase in the rate of tumor accumulation. Among the compounds of the present invention, the tumor accumulation property was changed depending on the difference in the number of the dye(s) labeled.

The highest rate of tumor accumulation was achieved in iTF (4.8) having a number of the dye(s) labeled of 4.8. The result was considered to be achieved by the best balance between hydrophilicity and hydrophobicity of each of the compounds to the rate of tumor accumulation. When the number of the dye(s) labeled exceeded the above value, it was considered that the entire hydrophobicity of each of the compounds was increased to promote protein adsorption in blood or to induce modification of the transferrin by itself, thereby reducing the retentivity in blood to result in a reduction in the rate of tumor accumulation.

The tumor/blood ratio was increased in the range from 3.5 times to even 11 times the tumor/blood ratio of each of ICG and Alexa Fluor 680-TF (2.0) in Comparative Examples. The reason why the result was obtained was because iTF of the present invention was low in the residual rate in blood while exhibiting a higher rate of tumor accumulation. In other words, it was meant that each of the compounds of the present invention was high in tumor accumulation retentivity. The result also supposed a high incorporation ability in a tumor cell.

As is clear from the imaging contrast in Table 4, a maximum tumor/blood ratio of 3.3 was achieved in iTF (4.8) having a number of the dye(s) labeled of 4.8. From the foregoing result, it was shown that iTF(s) according to Examples of the present invention were each a contrast agent for photoacoustic imaging that could allow for high sensitive and high tumor-selective tumor photoacoustic imaging.

TABLE 5

| Sample name | Rate of tumor accumulation (% ID/g) | Residual rate in blood (% ID/g) | Tumor/blood ratio |
|---|---|---|---|
| ICG | 0.0 | 0.1 | 0.1 |
| iTF (2.0) | 1.8 | 2.8 | 0.7 |
| iTF (4.8) | 7.1 | 2.1 | 3.3 |
| iTF (7.0) | 4.8 | 1.8 | 2.7 |
| iTF (8.3) | 2.1 | 0.7 | 2.9 |
| iTF (8.4) | 0.8 | 0.4 | 1.9 |
| AlexaFluor680-TF (2.0) | 0.6 | 2.8 | 0.2 |

The contrast agent for photoacoustic imaging according to the present invention includes a compound in which transferrin and a near-infrared dye having absorption in the near-infrared wavelength region, such as ICG, are bound, and therefore the contrast agent is high in tumor accumulation property and high in the photoacoustic signal intensity generated from a tumor as compared with ICG singly administered. The transferrin has the property of being incorporated in a cancer cell by a transferrin receptor, and as a result, has the effect of increasing the tumor/blood ratio.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-059617, filed Mar. 23, 2015, which is hereby incorporated by reference herein in its entirety.

What is claimed is:

1. A contrast agent comprising a compound represented by formula (I-1):

TF–(D)n  (I-1), wherein, in the formula (I-1), TF represents transferrin, n is 4.8 to 7.0, and D represents formula (d5) or formula (d6):

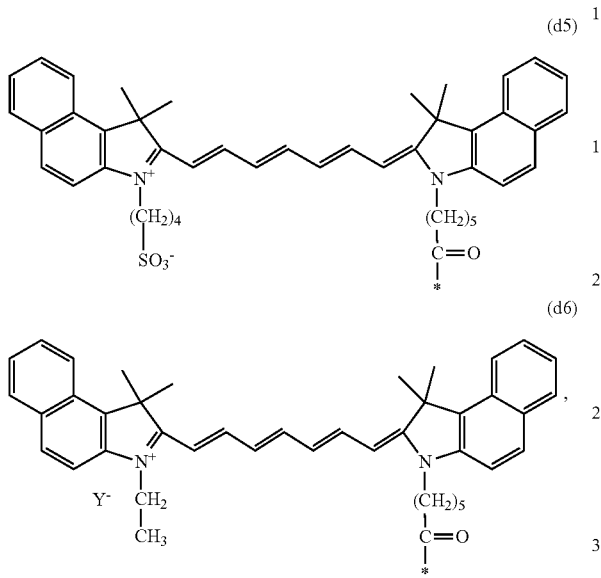

wherein, in the formulae (d5) and (d6), * represents a binding bond bound to the transferrin, and
wherein, in the formula (d6), Y⁻ represents a halogen ion or an organic acid ion.

2. A contrast agent comprising a compound represented by formula (I-1):

TF–(D)n  (I-1), wherein, in the formula (I-1), TF represents transferrin, D represents a near-infrared dye of formula (d5), and n is 4.8 to 7.0:

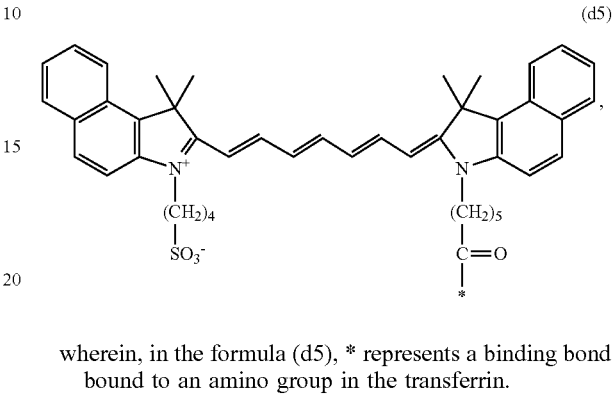

wherein, in the formula (d5), * represents a binding bond bound to an amino group in the transferrin.

3. The contrast agent according to claim 1, wherein the transferrin is any of human transferrin, a variant of human transferrin, a fragment of human transferrin, and a fragment of the variant of human transferrin.

4. The contrast agent according to claim 1, further comprising a capturing molecule.

5. The contrast agent according to claim 1, further comprising a dispersion medium, wherein the contrast agent is suitable for photoacoustic imaging.

6. The contrast agent according to claim 5, further comprising an additive.

* * * * *